(12) United States Patent
Minson

(10) Patent No.: US 8,083,672 B2
(45) Date of Patent: Dec. 27, 2011

(54) LARYNGOSCOPE

(76) Inventor: Matthew Minson, Arlington, VA (US)

( * ) Notice: Subject to any disclaimer, the term of this patent is extended or adjusted under 35 U.S.C. 154(b) by 965 days.

(21) Appl. No.: 11/868,299

(22) Filed: Oct. 5, 2007

(65) Prior Publication Data

US 2008/0167530 A1 Jul. 10, 2008

Related U.S. Application Data

(60) Provisional application No. 60/828,383, filed on Oct. 6, 2006.

(51) Int. Cl.
*A61B 1/32* (2006.01)
(52) U.S. Cl. .......................................................... 600/190
(58) Field of Classification Search .................. 600/185, 600/188, 190, 191, 194, 196, 199–210, 214; 606/190, 191, 196, 198
See application file for complete search history.

(56) References Cited

U.S. PATENT DOCUMENTS

| | | | |
|---|---|---|---|
| 4,517,964 A | 5/1985 | Upsher | |
| 4,570,614 A | 2/1986 | Bauman | |
| 4,573,451 A | 3/1986 | Bauman | |
| 4,832,020 A * | 5/1989 | Augustine | 128/207.14 |
| 5,036,835 A | 8/1991 | Filli | |
| 5,070,859 A | 12/1991 | Waldvogel | |
| 5,355,870 A | 10/1994 | Lacy | |
| 5,498,231 A | 3/1996 | Franicevic | |
| 5,651,760 A | 7/1997 | Upsher | |
| 5,702,351 A | 12/1997 | Bar-Or | |
| 5,938,591 A * | 8/1999 | Minson | 600/191 |

* cited by examiner

*Primary Examiner* — Eduardo C Robert
*Assistant Examiner* — Tara Carter
(74) *Attorney, Agent, or Firm* — Davidson Berquist Jackson & Gowdey, LLP

(57) ABSTRACT

The present invention is a self-retaining laryngoscope composed of a palate brace or blade, a slider, and a tongue blade. The angulated tongue blade puts less force on the blade, reduces trauma, and is not conducive for mechanical failure. The slider interacts with the tongue blade by widening the opening of the mouth, and acts as a bite block. The fenestrated palate blade provides an unobstructed view of the vocal cords during intubation, and allows removal of the laryngoscope over the endotracheal tube without displacing it. The result is a laryngoscope that requires only one hand to use properly, and has superior retraction due to its shape.

22 Claims, 7 Drawing Sheets

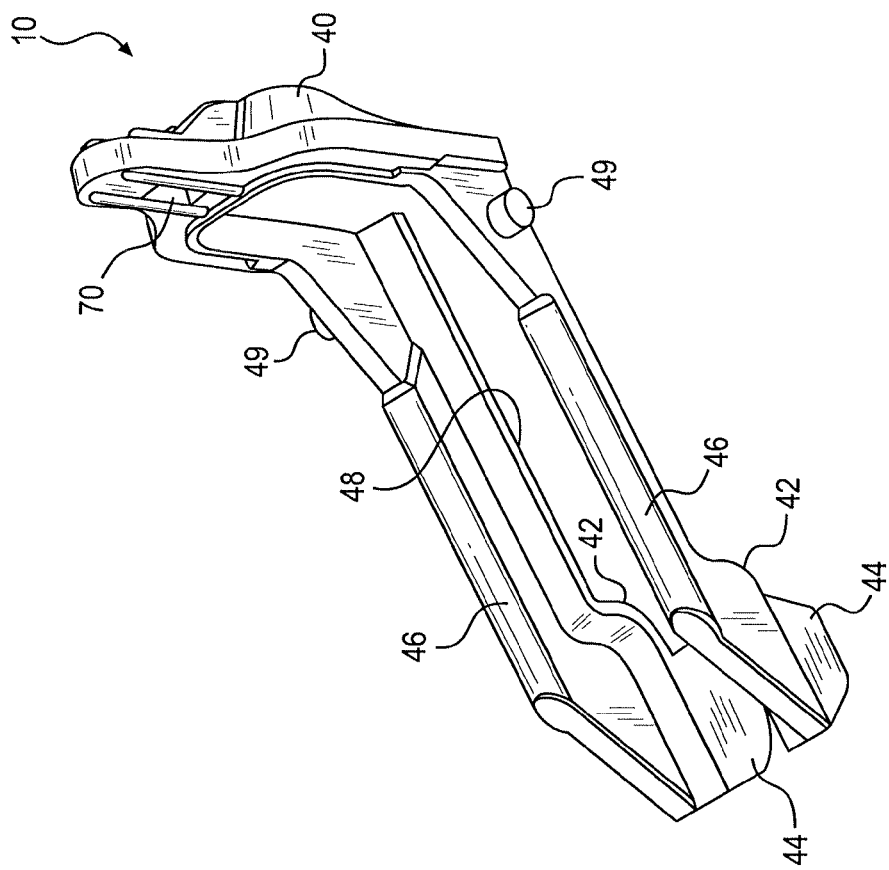
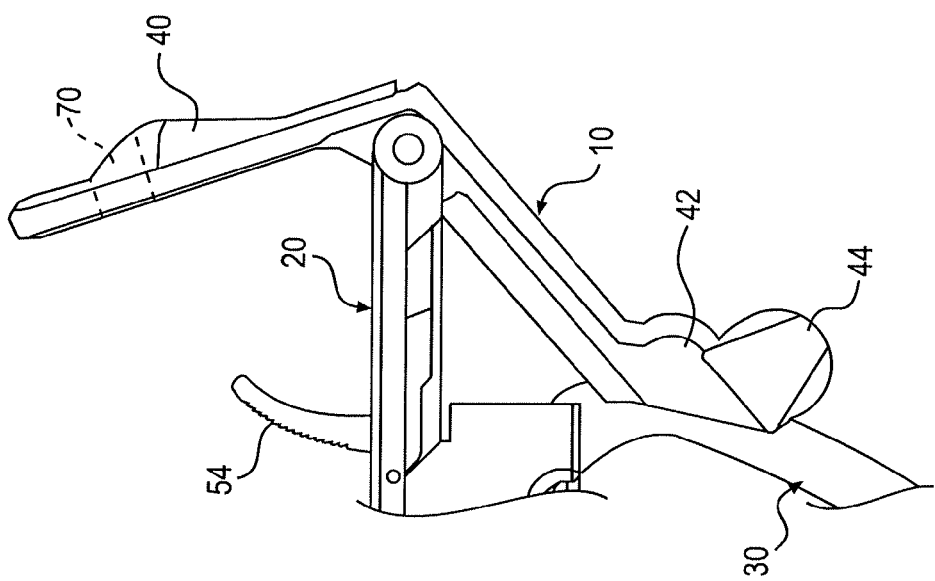
FIG. 4B
FIG. 4A

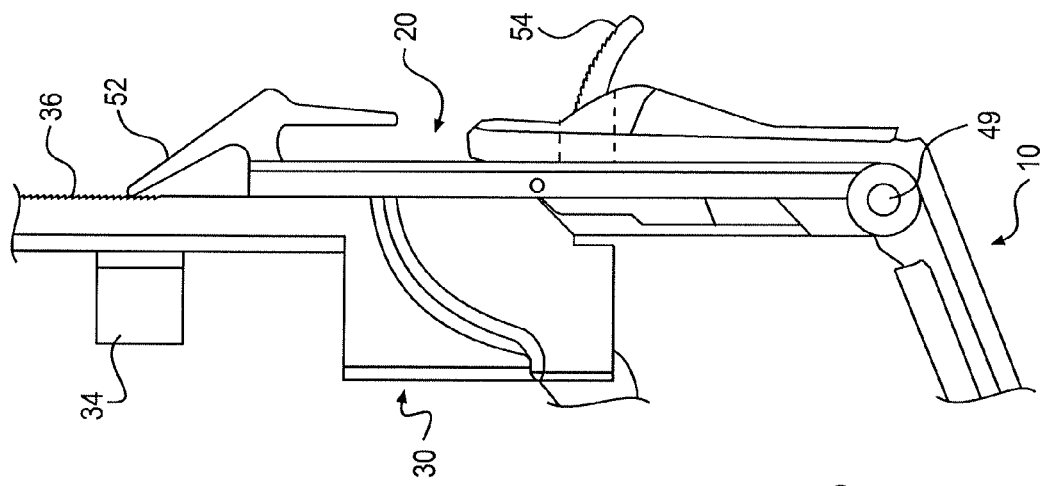
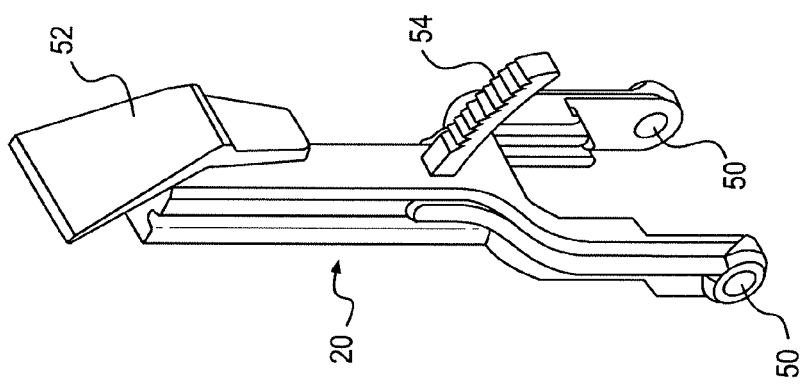
FIG. 5B
FIG. 5A

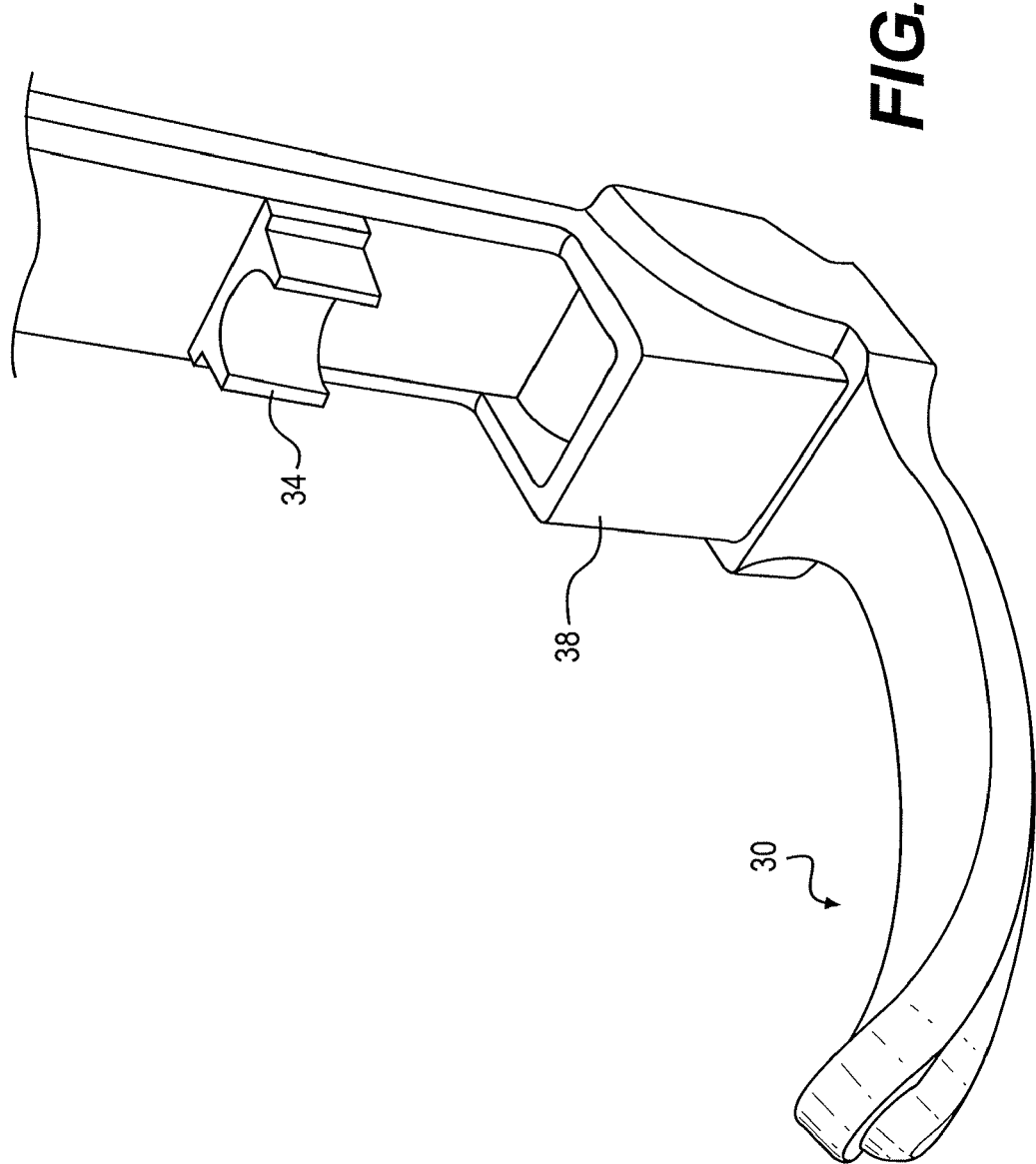

LARYNGOSCOPE

CITATION TO PARENT APPLICATION

This is a non-provisional application which claims priority, pursuant to 35 U.S.C. 119, to U.S. provisional application Ser. No. 60/828,383, filed 6 Oct. 2006.

BACKGROUND OF THE INVENTION

1. Field of the Invention

The present invention relates to medical instruments, and more particularly to an improved laryngoscope.

2. Background Information

The early need to visualize the larynx was for surgical purposes. As a medical student in 1829, Benjamin Guy Babington created a "glottiscope." One shank held down the tongue while the other was positioned along the palate. Sunlight provided the illumination for a view of the glottis. The glottiscope was later termed the laryngoscope by his contemporary, Thomas Hodgkins. In 1844, surgeon John Avery developed a head-mounted mirror that reflected candlelight onto a mirror housed within a speculum. But it was Manual Garcia (1805-1906), a professor of singing at the Royal Academy of Music in London, who is generally credited with the discovery of laryngoscopy. In 1854, he utilized a dental mirror in combination with a hand-held mirror reflecting sunlight to visualize his own larynx and trachea during inspiration and vocalization. At the age of 100, he was honored by the most prominent laryngologists of his time as the Father of laryngology. A laryngology clinic was established in Vienna in 1870 and minor surgical procedures were performed under visual control. British surgeon William Macewen was the first to intubate the larynx for surgical purposes. He practiced blind, digital intubation on cadavers and eventually employed this technique to perform a composite resection in 1878. Pediatrician Joseph O'Dwyer worked at New York City's Foundling Asylum, where he developed instruments to enable tracheal intubation that saved the lives of hundreds of children suffocating from diphtheria.

Hans Kuhn modified O'Dwyer's instruments and created a long, flexible metal endotracheal tube and introducer, but his method still depended upon blind insertion, as light sources were inadequate to permit progress in direct laryngoscopy (DL). In 1895, Alfred Kirstein learned of an inadvertent tracheal insertion of an esophagoscope, and proceeded to develop a rigid laryngoscope with transmitted light. This consisted of a lamp within the handle, focused on a lens and redirected through the scope by a prism. Chevalier Jackson subsequently modified Kirstein's laryngoscope by providing distal illumination with a tungsten bulb. In 1913, Henry Janeway devised an open-sided laryngoscope with battery-operated distal illumination specifically for endotracheal intubation.

In 1941, Robert Miller introduced a new, longer, lower profile laryngoscope, which was designed to pick up the epiglottis. This blade required limited mouth opening but also left little space to manipulate the endotracheal tube (ETT). In 1943, Robert Macintosh described a curved blade to elevate the epiglottis by exerting its force on the base of the tongue. He believed that reducing contact with the epiglottis would be less stimulating and provide more room for manipulation of the ETT. Although both blades have been variously modified in the interim, they continue to dominate the field of laryngoscopy. Yet they both fail to provide an adequate glottic view in a small but significant number of patients.

Although there have been advancements in larygoscopy, e.g., fiber optics, varying techniques, lighted wands, and a number of technological modalities, the basic laryngoscope, which is far and away the most utilized instrument, has not materially improved since the early 1940s.

After years of clinical studies, it is clear that positioning alone does not align the mouth, pharyngeal and laryngeal axes and that force must be applied to achieve this. In any situation involving the care of a critically ill or injured person, the first consideration is always establishment and maintenance of the airway. It is estimated that failed intubation, especially in the emergency and austere environment, is the leading "preventable" cause of morbidity and mortality. In the pre-hospital environment, it is estimated that intubation success rates vary from approximately 85-95%. This compares to the approximate 99% success rates in hospitals. The main reasons for such a disparity are training, experience, resources, and technique.

The inability to see the larynx generally results in multiple or prolonged laryngoscopic attempts with increasing force, and is associated with esophageal, pharyngeal and dental injury, arterial desaturation, hemodynamic instability and unplanned intensive care unit admissions. An American Society of Anesthesiologists Task Force's definition of a difficult laryngoscopy states that "it is not possible to visualize any part of the vocal cords after multiple attempts" and a difficult tracheal intubation as one which "requires multiple attempts." Though successfully accomplishing intubation is important, it is not enough. Intubation without an adequate laryngeal view should be regarded as a "near-miss," which is incentive enough to improve airway management techniques and reduce reliance upon luck and multiple or forceful laryngoscopies.

The laryngoscope of the future will provide predictable laryngeal exposure and consistently successful intubation. It will be easy to learn, quickly performed and will impose less stress upon the patient. It will be inexpensive to acquire and robust enough to withstand the hostile environment of the pre-hospital setting as well as the operating room. It will not depend on sunlight for reliable laryngeal illumination.

Presently known prior art includes the following:

U.S. Pat. No. 4,570,614, which issued to Bauman on Feb. 18, 1986, teaches a laryngoscope with a single disposable nonmetallic blade, a light source disposed within the handle and a light conductor disposed adjacent to and held by the blade. Typical of the prior art, this apparatus requires two hands to operate, and perhaps even two caregivers, if the patient's mouth and head must be stabilized. Lacy (U.S. Pat. No. 5,355,870) and Bar-Or et al. (U.S. Pat. No. 5,702,351) also teach disposable plastic single blades used in combination with a light source in a laryngoscope.

U.S. Pat. No. 4,573,451, which issued to Bauman on Mar. 4, 1986, teaches a laryngoscope blade which has a tip that is capable being bent or flexed in the direction of the handle of the laryngoscope. This allows the patient's epiglottis to be lifted to expose the patient's larynx. This is a single blade instrument. It is provided with a ratchet lock to maintain the bend in the tip. This instrument can bend in only one direction, to lift the epiglottis. Locking the laryngoscope blade in an operable position is also shown in U.S. Pat. No. 5,651,760, but this lock/unlock mechanism functions to enable the instrument to be compact when it is not in use.

U.S. Pat. No. 5,036,835, which issued to Filli on Aug. 6, 1991, teaches a slideably adjustable spatula portion in the laryngoscope blade. The function of this spatula is to act as a tongue depressor to facilitate inspection of the pharynx and larynx, or the insertion of an anesthetic breathing tube. This apparatus uses a single blade with a sliding part, which does not lock in position.

U.S. Pat. No. 5,070,859, which issued to Waldvogel on Dec. 10, 1991, teaches a laryngoscope that incorporates a dynamometer in order to measure the force used by the caregiver to examine the patient. This invention is an attempt to avoid trauma to the patient that can occur using prior art apparatus.

U.S. Pat. No. 4,517,964, which issued to Upsher on May 21, 1985, teaches a dual bladed laryngoscope, wherein one conventional blade carries its own light source and the second blade is a light guide for a second light source in the handle of the instrument.

U.S. Pat. No. 5,498,231, which issued to Franicevic on Mar. 12, 1996. This apparatus is the current state of the art in the field of laryngoscopes. Franicevic teaches a reusable laryngoscope for use "in difficult intubation due to malformation of the jaws, tongue, pharynx, larynx or neck as a result of trauma, edema, inflammation or congenial anomalies." This laryngoscope has a hollow body terminating at its distal end in a pair of opposed blades that can be spread apart by the caregiver. An endotracheal tube slides through the hollow tube in the center of the instrument. Light conducting means are provided to illuminate the larynx. The device includes a fiberoptic optical system for inspecting the larynx during intubation. Franicevic is an improvement on the "bendable tip" of Bauman, cited above. The single distal spreading of the "beak" taught by Franicevic allows some lifting of the soft tissue, but it does nothing to open the mouth or depress the tongue. Franicevic teaches a bias spring to keep the distal blades closed when they are not positively spread apart by the caregiver. This apparatus is not locking or self-retaining in the airway. It also is not disposable and its complex mechanism makes it difficult to adequately sterilize.

The closest prior art known to the present inventor is U.S. Pat. No. 5,938,591, which issued to Minson, the present invention, on Aug. 17, 1999. The '591 patent is a disposable self-retaining laryngoscopes used for orally intubating a patient with an endotracheal tube. However, this design ultimately failed in almost every configuration. The current invention is not similar to the '591 patent: the tongue blade, the palate blade and slider have all been changed significantly. Lengths, angles, and the configuration of the invention have all substantially changed relative to the '591 patent. For example, the fenestration of the improved palate blade allows removal of the laryngoscope over the endotracheal tube without displacing it. This is not possible with the '591 patent.

Despite all of the benefits from the limited improvements of the basic laryngoscope over the decades and the alternatives thereof, there still exists the need for an improvement in laryngoscopic technology at the most basic level to address the aforementioned issues. The number of different variations of laryngoscope found in the prior art is a good indication that many experts skilled in this art have tried to find solutions to these problems. Current technology requires that individuals "retract" the airway with one hand while attempting to intubate with the other. In fact, four hands may be needed to hold the head and mouth of the patient, operate the laryngoscope and intubate the patient. Therefore, an improved laryngoscope is needed that incorporates 1) hands-free application for simultaneous suction and intubation, which is especially important in trauma, and 2) improved and broader illumination. Until now, such an invention does not exist.

SUMMARY OF THE INVENTION

In view of the foregoing, it is an object of the present invention to provide an improved laryngoscope.

It is another object of the present invention to provide an improved laryngoscope that exhibits hands-free application.

It is another object of the present invention to provide an improved laryngoscope with an improved and broader illumination.

It is another object of the present invention to provide an improved laryngoscope with a self-retaining mechanism.

It is another object of the present invention to provide an improved laryngoscope consisting in part of clear plastic.

It is another object of the present invention to provide an improved laryngoscope to be strong, inexpensive, and simple to use.

It is another object of the present invention to provide an improved laryngoscope that facilitates intubation more readily than pre-existing laryngoscopes.

It is another object of the present invention to provide an improved laryngoscope to incorporate a palate blade fenestration, which allows some flexion and presents a "target aperture."

It is another object of the present invention to provide an improved laryngoscope to provide an improved angle of the tongue blade.

It is another object of the present invention to provide an improved laryngoscope to provide a neck attachment for a penlight illumination source.

It is another object of the present invention to provide an improved laryngoscope with three different sizes—small, medium, or large.

It is another object of the present invention to provide an improved laryngoscope that allows overlap or displacement of the mass of the tongue from the sight line in the center of the mouth.

It is another object of the present invention to provide an improved laryngoscope that reduces trauma and potential mechanical failure by putting less force on the blade.

It is another object of the present invention to provide an improved laryngoscope in which attachment and removal of the light source is considerably easier than the prior art.

It is another object of the present invention to provide an improved laryngoscope by providing superior retraction due to its shape.

It is another object of the present invention to provide an improved laryngoscope that allows retraction and wider opening of the mouth and airway.

It is another object of the present invention to provide an improved laryngoscope with a shortened blade that keeps the invention off the patient's teeth and not conducive to tissue injury.

It is another object of the present invention to provide an improved laryngoscope that provides an unobstructed view of the vocal cords during intubation.

It is another object of the present invention to provide an improved laryngoscope that allows removal of the laryngoscope over the endotracheal tube without displacing it.

In satisfaction of these and related object, the present invention is a self-retaining laryngoscope, which is an improvement over every known prior device or method that addresses the problem of establishing and maintaining the airway, especially in trauma situations An improved laryngoscope of the present invention affords hands-free application, which is necessary to allow simultaneous suction and intubation. This is especially important in trauma situations. The improved laryngoscope also has an improved and broader illumination.

The benefits provided by embodiments of the improved laryngoscope of the present invention are a revolutionary laryngoscope that is strong, reliable, inexpensive, and simple to use, while facilitating intubation more readily and safer than any pre-existing laryngoscope.

BRIEF DESCRIPTION OF THE DRAWINGS

FIG. 4A shows the palate blade in a closed position on the slider with portions cut away.

FIG. 4B illustrates the palate blade component of the preferred embodiment of the present invention.

FIG. 5A illustrates the slider component of the preferred embodiment of the present invention.

FIG. 5B shows the slider with the palate blade in an open position with the ratchet engaged and a portion of the tongue blade.

FIG. 6 shows a perspective view of the tongue blade.

DETAILED DESCRIPTION OF THE PREFERRED EMBODIMENT

Figure 1:
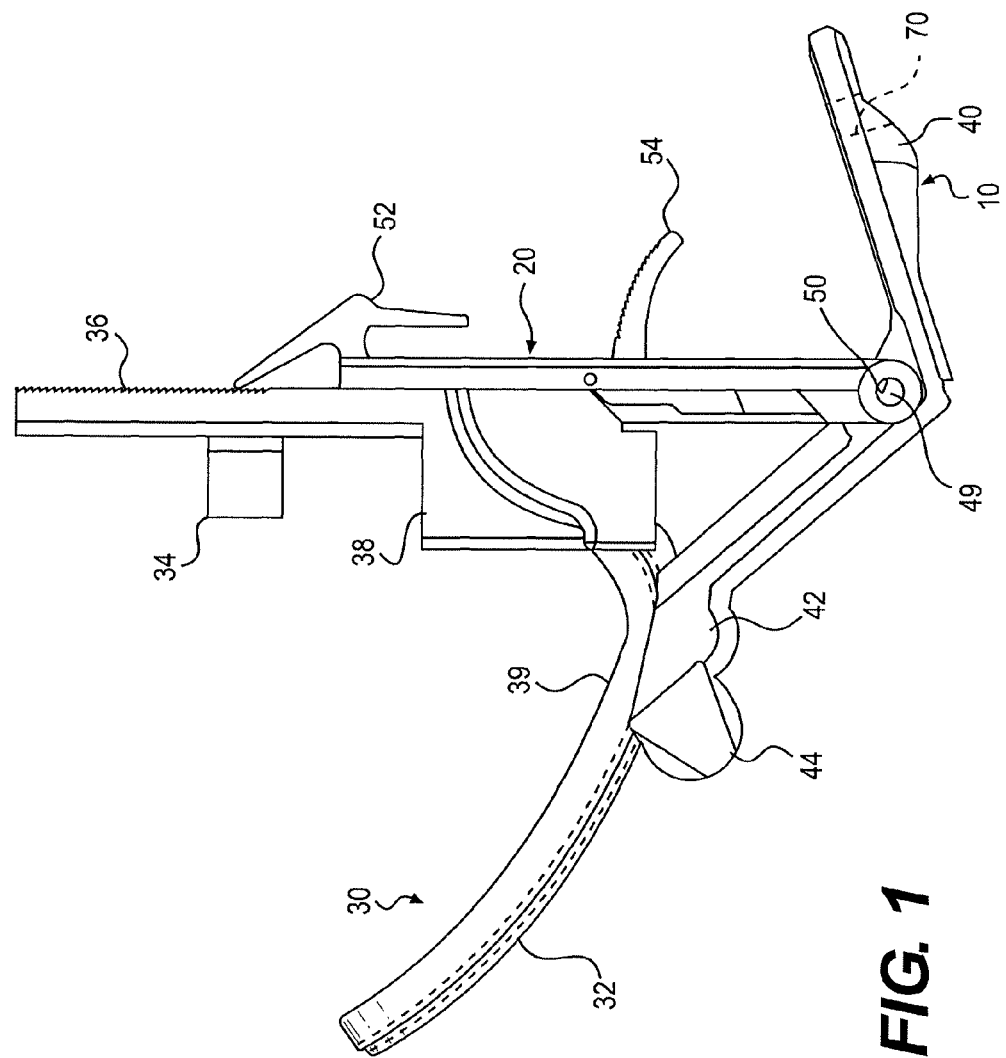
FIG. 1 illustrates the side view of the closed position of the preferred embodiment of the present invention.

Referring to FIG. 1, which illustrates the closed position of the preferred embodiment of the present invention, the self-retaining laryngoscope is composed of three components: 1) the palate brace or blade 10, 2) the slider 20, and 3) the tongue blade 30.

The tongue blade 30 includes the angulated blade 39 with light conduction "rail" 32, the light source clip 34, an interface 38, and the teeth 36 for interaction with the slider thumb piece 52 to allow retraction and wider opening of the mouth and airway.

The configuration of the tongue blade 30 has been shown during clinical trials to require an angulation 39 of the blade. A straight blade does not conform to the natural curve of the airway. The new angle 39 of the present invention in its preferred embodiment was clinically tested for optimization, and was found to be a curve of approximately 60 degrees. It is sized to be either small, medium, or large.

The narrowing of the width of the tongue blade 30 to 2 centimeters is an improvement over the prior art—including the '591 Minson patent—as it allows less material to be used and allows overlap or displacement of the mass of the tongue from the sight line in the center of the mouth. It also puts less force on the blade 10, reducing trauma, and potential mechanical failure. The light conduction rail or light dissemination platform 32 on the inferior aspect of the tongue blade 30 improves illumination as well.

Also, and specifically with respect to the '591 Minson patent vis-à-vis the present invention, the tongue blade of the '591 patent was wider than the width of the tongue. The '591 patent failed as it was thin and could not support the stress of displacing the mass of the tongue without bending or fracturing. It also failed in the retraction of the tongue.

The light source clip 34 on the tongue blade 30 is unique in that it is not a box configuration such that attachment and removal of the light source is considerably easier.

When looking at the tongue blade 30 "end on," the shape is similar to an inverted pyramid. This represents a far superior alteration or configuration as it allows superior retraction due to its shape.

Figure 2:
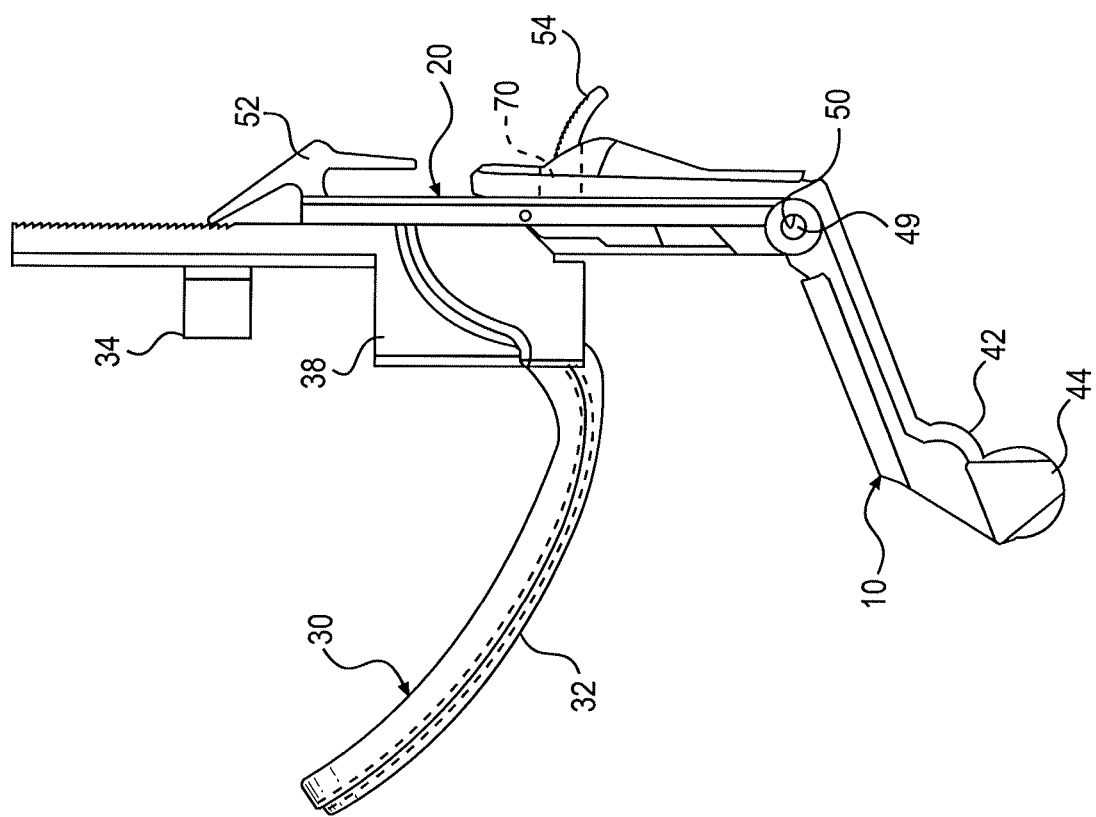
FIG. 2 illustrates the side view of the open or retaining position of the preferred embodiment of the present invention.

Referring to FIG. 2, which illustrates the open or retaining position of the preferred embodiment of the present invention, shows the position of the slider 20 when fully engaged, and the palate brace or blade 10 when fully engaged.

Figure 3:
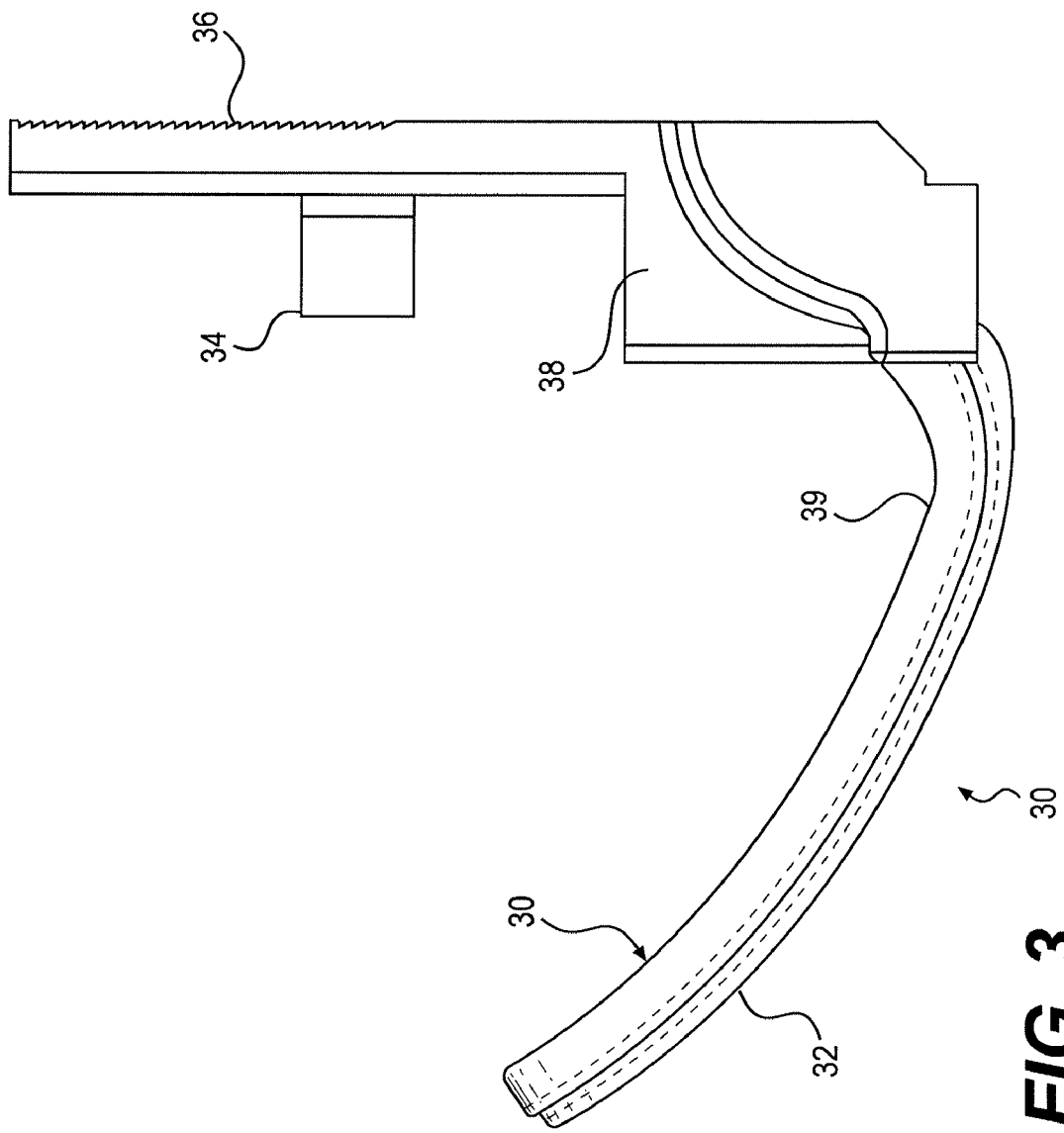
FIG. 3 illustrates the tongue blade component of the preferred embodiment of the present invention.
Figure 7:
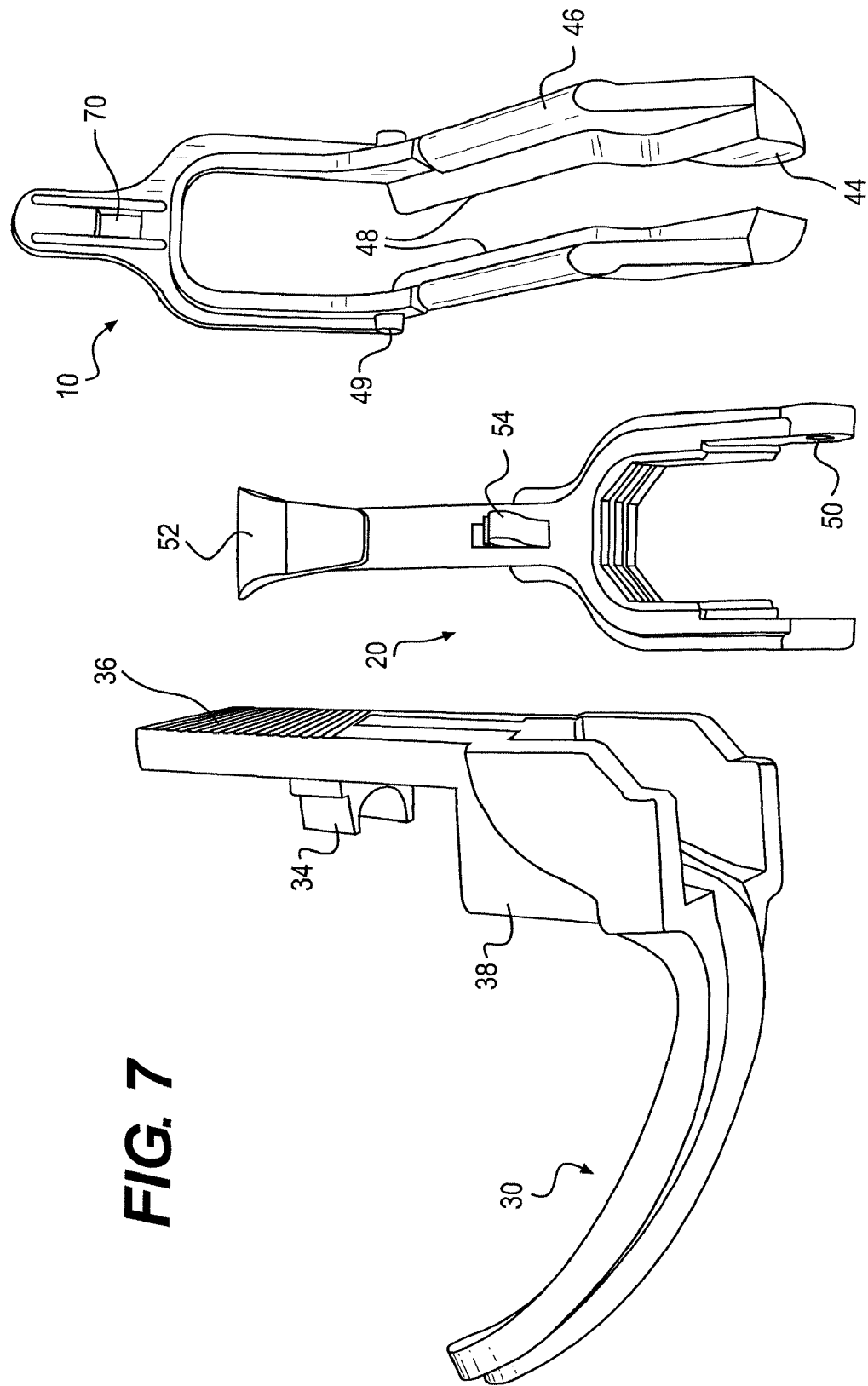
FIG. 7 shows perspective views of each of the tongue blade, the slider and palate blade.

Referring to FIG. 3, which illustrates the tongue blade 30 of the preferred embodiment of the present invention, the tongue blade 30 includes the angulated 39 blade with light conduction "rail" 32, the light source clip 34, and the teeth 36 for interaction with the slider thumb piece 52 to allow retraction and wider opening of the mouth and airway.

The angle 39 of the curved tongue blade 30 from the vertical plane of the tongue blade 30 piece is critically important and another distinguishing characteristic vis-à-vis the prior art. The optimal angle is 30 degrees from the vertical. Flat blades of prior art do not produce the retraction necessary to facilitate the necessary visualization of the vocal cords.

Also, the distal end, which is the farthest insertion into the laryngeal vault, of the tongue blade 30 is rounded. This roundness at the distal end minimizes soft tissue trauma. The tapering of the tongue blade 30 at the most distal end also effectively improved visualization of the vocal cords.

Specifically, based on clinical trials, the optimum width of the tongue blade 30 is one centimeter in width, which proved optimal for retraction and allowed redundant tissue to be retracted in the "locked" configuration. It also allowed the inverted pyramidal shape of the tongue blade 30 to support more force with less material, and thus allowing more operating space in the oropharynx. The length of the blade 30 would be determined by the size of the patient, which, according to the results of the study and is the preferred embodiment, is a 20:2 or 10:1 length-to-breadth ratio. The reduction of the width of the blade of the present invention represents a critical component and a distinguishing characteristic from the prior art. The wider blades of the prior art, including the '591 patent, engaged the force of the tongue in a greater area of surface interaction and attempted to retract comprehensively across the entirety of the tongue. This can and usually creates a critical stress and even mechanical failure of some of the prior art. The narrow width of the preferred embodiment of the present invention allows a retraction of the tongue and soft tissue without being stressed to a breaking point.

Referring to FIG. 4, which illustrates the palate brace or blade 10 of the preferred embodiment of the present invention, the structure of the palate brace or blade 10 is unique. In some prior art, the palate blade is flat, which would injure tissue and would not retract adequately. Some prior art palate blades, which also levered on the soft palate and could have injured the tissue, were made of single solid pieces, which would effectively block visualization. The palate steps 42 (configuration have been built up with "blocks") in the shortened blade of the preferred embodiment leverage against the hard palate and keep the device off the patient's teeth and prevents soft tissue injury.

Furthermore, the palate brace or blade 10 provides the leveraging capability against the bony palate. The lateral aspect of the palate brace or blade 10 has been built up or thickened in order to sustain greater stress and force, and thereby reducing the potential for mechanical failure. The palate brace or blade 10 is composed of a fenestrated blade that conforms via the "steps" 42 to the palate and the fenestration 48 that provides an unobstructed view of the vocal cords during intubation. The configuration of the palate steps 42 in the shortened blade effectively keeps the device off of the patient's teeth. The fenestration 48 of the palate brace or blade 10, which is wider than an "8" endotracheal tube, allows visualization of the vocal cords during intubation, and also allows removal of the laryngoscope over the endotracheal tube without displacing it. This is a substantial improvement over prior art.

The pegs 49 articulate with the peg apertures 50 on the slider 20 and the ratchet 54 articulates through palate blade aperture 70 with the retaining capacity of the ratchet on the slider 20. The struts 40 on the palate brace or blade 10 have improved the strength of the mechanism to bear more stress, which reduces the risk of mechanical failure. In addition, the lateral aspect of the palate brace or blade 10 has been built up to further sustain greater stress and force, which furthermore reduces the potential for mechanical failure.

Referring to FIG. 5, which illustrates the slider 20 of the preferred embodiment of the present invention, the slider 20 has three interactive applications. The first is the thumb piece 52, which interacts with the tongue blade 30 widening the opening of the mouth, and acts as a bite block. The second is the ratchet 54, which interfaces with the palate blade aperture 70 to "open" the airway. The third is the pin aperture 50, which allows the palate blade 10 to rotate and interact with the tongue blade 30. The slider 20 has been improved over prior art. The ratchet 54 may bear coarser teeth 36 or a slot and groove mechanism to assure the retraction. The struts 40 on the upper rear area of the palate brace or blade 10 have improved the strength of the mechanism so it can bear more stress, which reduces the risk of mechanical failure.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A laryngoscope having a tongue member and a palate blade member interconnected by a slider member that is adjustably attached to a portion of the tongue member and is pivotally connected at a bottom end to a middle portion of the palate blade member;

the tongue member including a vertical body portion having front and rear sides, a tongue blade extending in a distal direction from the front side adjacent a bottom of the vertical body, the tongue blade having a length to width ratio of about 10:1 and a cross-sectional shape substantially in the form of an inverted pyramid, said tongue blade being positioned at an acute angle relative to the vertical body portion, the vertical body portion further including a clip member on the front side and a set of horizontal grooves on an upper portion of the rear side;

the palate blade member having a rear portion and a front portion, the rear portion having a upper section, and a lower section formed with a of spaced apart depending arms, the front portion comprised of two legs that extend from a bottom portion of the spaced apart depending arms, respectively, the two legs being spaced apart to define an open fenestration there between, a distal end of each of the two legs including a depending step and block configuration;

the slider member including an upper portion having a latch member that will releasably interact with the horizontal grooves on the vertical body, a centrally located, rearwardly extending ratchet that will releasably interact with an aperture provided in the upper section of the palate blade to provide hands free adjusting of the relative position between the palate blade and the tongue member.

2. The laryngoscope as in claim 1 wherein the tongue blade has a width of about 2 centimeters.

3. The laryngoscope as in claim 1 wherein the tongue blade provides a light conduction path.

4. The laryngoscope as in claim 1 wherein the acute angle is about 60°.

5. The laryngoscope as in claim 4 wherein acute angle ranges from about 30° to about 60°.

6. The laryngoscope as in claim 1 wherein the depending step and block formation includes a downwardly extending step designed to interfit behind teeth in a mouth and the step interacts against a palate portion of a mouth.

7. The laryngoscope as in claim 1 wherein a lateral aspect of each of the two legs is provided with reinforcing to permit the legs to sustain stress associated with opening the laryngoscope and to position the tongue to provide an open channel to the larynx.

8. The laryngoscope as in claim 1 wherein a cup structure is provided below the clip and adjacent a proximal portion of the tongue blade at the connection with the vertical body portion.

9. The laryngoscope as in claim 1 wherein a distal end of the tongue blade is rounded and tapered.

10. The laryngoscope as in claim 1 wherein the tongue member has a width of about 1 centimeter.

11. The laryngoscope as in claim 1 wherein the length of each of the two arms is less than the length of the tongue blade.

12. A laryngoscope comprising:

a tongue blade member having a proximal tongue blade extending from a distal body portion at an acute angle;

a palate blade member having a proximal handle segment, a distal palate blade segment, and a palate blade pivot point residing there between; and a support member adjustably attached to the distal body portion and pivotally connected to said palate blade member at said palate blade pivot point;

said distal palate blade segment comprising two spaced apart arm members having an open fenestration there between; and said proximal handle segment being operatively connectable with a ratchet member provided on the support member to releasably hold a relative position established between the tongue blade member and a pivoted condition of the palate blade member.

13. The laryngoscope as in claim 12 wherein the tongue blade has a width of ranging from about 1 centimeter to about 2 centimeters.

14. The laryngoscope as in claim 12 wherein the tongue blade provides a light conduction path.

15. The laryngoscope as in claim 12 wherein the acute angle is about 60° relative to an axis of the distal body portion.

16. The laryngoscope as in claim 12 wherein acute angle ranges from about 30° to about 60°.

17. The laryngoscope as in claim 12 further including a depending step and block formation at a distal end of the two spaced apart arm members which includes a downwardly extending step designed to interfit behind teeth in a mouth and the step interacts against a palate portion of a mouth.

18. The laryngoscope as in claim 12 wherein a lateral aspect of each of the two spaced apart arm members is provided with reinforcing to permit each of the two spaced apart arm members to sustain stress associated with opening the laryngoscope and to position the tongue to provide an open channel to the larynx.

19. The laryngoscope as in claim 12 wherein a clip is provided on the distal body portion and a cup structure is provided there below and adjacent a proximal portion of the tongue blade at the connection with the distal body portion.

20. The laryngoscope as in claim 12 wherein a distal end of the tongue blade is rounded and tapered.

21. The laryngoscope as in claim 12 wherein the tongue member has a length to width ratio of about 10:1.

22. The laryngoscope as in claim 12 wherein the tongue blade has a cross-sectional shape substantially in the form of an inverted pyramid.

* * * * *